US012649716B2

(12) United States Patent
Hwang et al.

(10) Patent No.: US 12,649,716 B2
(45) Date of Patent: Jun. 9, 2026

(54) SILICON COMPOUND AND METHOD OF MANUFACTURING INTEGRATED CIRCUIT DEVICE USING THE SAME

(71) Applicant: SAMSUNG ELECTRONICS CO., LTD., Suwon-si (KR)

(72) Inventors: Sunhye Hwang, Suwon-si (KR); Sunggi Kim, Daedeok-gu (KR); Yeonghun Kim, Daedeok-gu (KR); Gyunsang Lee, Daedeok-gu (KR); Jihyun Lee, Suwon-si (KR); Gyuhee Park, Suwon-si (KR); Seung Son, Daedeok-gu (KR); Younjoung Cho, Suwon-si (KR); Byungkeun Hwang, Suwon-si (KR)

(73) Assignees: SAMSUNG ELECTRONICS CO., LTD.; DNF Co., Ltd.

(*) Notice: Subject to any disclaimer, the term of this patent is extended or adjusted under 35 U.S.C. 154(b) by 391 days.

(21) Appl. No.: 18/209,583

(22) Filed: Jun. 14, 2023

(65) Prior Publication Data

US 2023/0406822 A1 Dec. 21, 2023

(30) Foreign Application Priority Data

Jun. 17, 2022 (KR) ........................ 10-2022-0074337

(51) Int. Cl.
*C07D 207/46* (2006.01)
*C07D 265/32* (2006.01)
(Continued)

(52) U.S. Cl.
CPC ......... *C07D 207/46* (2013.01); *C07D 265/32* (2013.01); *C07D 403/12* (2013.01); (Continued)

(58) Field of Classification Search
None
See application file for complete search history.

(56) References Cited

U.S. PATENT DOCUMENTS 7,915,180 B2 3/2011 Gates et al.
8,097,932 B2 1/2012 Nguyen et al.
(Continued)

FOREIGN PATENT DOCUMENTS

JP 2003-151972 A 5/2003
WO WO 2014/152826 A1 9/2014

OTHER PUBLICATIONS

Erchak N P et al: "Methanolysis of 2-Furylsilane", Chemistry of Heterocyclic Compounds, vol. 46, No. 5, Jan. 1, 2010.
(Continued)

*Primary Examiner* — Asok K Sarkar
(74) *Attorney, Agent, or Firm* — Muir Patent Law, PLLC

(57) ABSTRACT

A silicon compound, a composition, and associated methods, the silicon compound being represented by Chemical Formula (1):

$$R1_m(OR2)_n(OR3)_{3-m-n}Si—O—SiR4_p(OR5)_q(OR6)_{3-p-q},$$ Chemical Formula (1)

wherein, in Chemical Formula (1), m, n, p, and q are each independently an integer of 0 to 3, and satisfy the following relations m+p≥1, m+n≤3, and p+q≤3, R1 is a heterocyclic group, R4 is a heterocyclic group, a carbon saturated group, or a carbon unsaturated group, and R2, R3, R5, and R6 are each independently a hydrogen atom, a C1-C7 alkyl group, a C2-C7 alkenyl group, a C3-C7 cycloalkyl group, or a C3-C7 cycloalkenyl group.

20 Claims, 10 Drawing Sheets

(51) Int. Cl.

| | |
|---|---|
| ***C07D 403/12*** | (2006.01) |
| ***H01L 21/02*** | (2006.01) |
| ***H10P 14/60*** | (2026.01) |
| ***H10P 14/692*** | (2026.01) |

(52) U.S. Cl.

CPC ...... *H10P 14/6339* (2026.01); *H10P 14/6686* (2026.01); *H10P 14/6687* (2026.01); *H10P 14/6927* (2026.01)

(56) References Cited

U.S. PATENT DOCUMENTS

| | | | |
|---|---|---|---|
| 8,227,358 B2 | 7/2012 | Wang et al. | |
| 9,212,420 B2 | 12/2015 | Lee et al. | |
| 9,677,178 B2 | 6/2017 | Spence et al. | |
| 10,283,348 B2 | 5/2019 | Wang et al. | |
| 10,703,915 B2 | 7/2020 | Lei et al. | |
| 2003/0091838 A1 | 5/2003 | Hayashi et al. | |
| 2005/0236694 A1 | 10/2005 | Wu et al. | |
| 2019/0249303 A1 | 8/2019 | Kuroda et al. | |
| 2020/0308416 A1* | 10/2020 | Lei | C23C 16/45536 |

OTHER PUBLICATIONS

Extended European Search Report issued Dec. 4, 2023 for corresponding EP Patent Application No. 23179857.0.

* cited by examiner

SILICON COMPOUND AND METHOD OF MANUFACTURING INTEGRATED CIRCUIT DEVICE USING THE SAME

CROSS-REFERENCE TO RELATED APPLICATION

This application is based on and claims priority under 35 U.S.C. § 119 to Korean Patent Application No. 10-2022-0074337, filed on Jun. 17, 2022, in the Korean Intellectual Property Office, the disclosure of which is incorporated by reference herein in its entirety.

BACKGROUND

1. Field

Embodiments relate to a silicon compound and a method of manufacturing an integrated circuit device by using the same.

2. Description of the Related Art

With the recent development of electronics technology, ultra-miniaturization of integrated circuit devices has been rapidly conducted. Accordingly, the size of a device area has been reduced and the aspect ratio of unit devices has been increased, and thus, technology for forming a silicon-containing film having a uniform thickness and excellent electrical properties has been considered.

SUMMARY

The embodiments may be realized by providing a silicon compound represented by Chemical Formula (1):

$R1_m(OR2)_n(OR3)_{3-m-n}Si—O—SiR4_p(OR5)_q(OR6)_{3-p-q}$, Chemical Formula (1)

wherein, in Chemical Formula (1), m, n, p, and q are each independently an integer of 0 to 3, and satisfy the following relations m+p≥1, m+n≤3, and p+q≤3, R1 is a heterocyclic group, R4 is a heterocyclic group, a carbon saturated group, or a carbon unsaturated group, and R2, R3, R5, and R6 are each independently a hydrogen atom, a C1-C7 alkyl group, a C2-C7 alkenyl group, a C3-C7 cycloalkyl group, or a C3-C7 cycloalkenyl group.

The embodiments may be realized by providing a composition for depositing a silicon-containing film, the composition comprising the silicon compound according to an embodiment.

The embodiments may be realized by providing a method of manufacturing an integrated circuit device, the method comprising forming a silicon-containing film on a substrate, by using a silicon compound represented by Chemical Formula (1):

$R1_m(OR2)_n(OR3)_{3-m-n}Si—O—SiR4_p(OR5)_q(OR6)_{3-p-q}$, Chemical Formula (1)

wherein, in Chemical Formula (1), m, n, p, and q are each independently an integer of 0 to 3, and satisfy the following relations: m+p≥1, m+n≤3, and p+q≤3, R1 is a heterocyclic group, R4 is a heterocyclic group, a carbon saturated group, or a carbon unsaturated group, and R2, R3, R5, and R6 are each independently a hydrogen atom, a C1-C7 alkyl group, a C2-C7 alkenyl group, a C3-C7 cycloalkyl group, or a C3-C7 cycloalkenyl group.

The embodiments may be realized by providing a method of manufacturing an integrated circuit device, the method including preparing a substrate having an active area and a device separation area; forming a gate dielectric film on the substrate; forming a gate electrode on the gate dielectric film; forming a gate structure by patterning the gate dielectric film and the gate electrode; and forming source/drain regions in the substrate at both sides of the gate structure, wherein forming the gate dielectric film includes forming a silicon compound adsorption layer on a surface of the substrate by supplying a silicon compound represented by Chemical Formula (1) onto the substrate; and forming a silicon oxide film by supplying a reaction gas to a resultant in which the silicon compound adsorption layer is formed, $R1_m(OR2)_n(OR3)_{3-m-n}Si—O—SiR4_p(OR5)_q(OR6)_{3-p-q}$, Chemical Formula (1)

wherein, in Chemical Formula (1), m, n, p, and q are each independently an integer of 0 to 3, and satisfy the following relations: m+p≥1, m+n≤3, and p+q≤3, R1 is a heterocyclic group, R4 is a heterocyclic group, a carbon saturated group, or a carbon unsaturated group, and R2, R3, R5, and R6 are each independently a hydrogen atom, a C1-C7 alkyl group, a C2-C7 alkenyl group, a C3-C7 cycloalkyl group, or a C3-C7 cycloalkenyl group.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
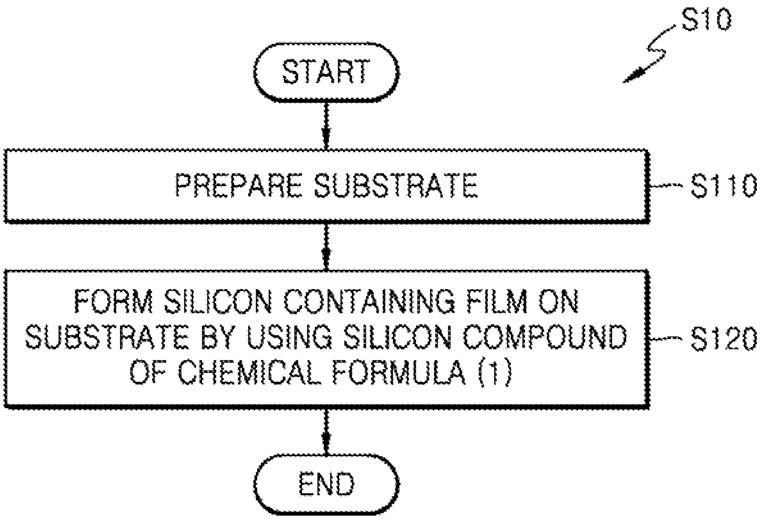
FIG. 1 is a flowchart showing a method of manufacturing an integrated circuit device, according to an embodiment.

In the specification, the term "substrate" used herein may mean a substrate by itself, or a stack structure including a substrate and a certain layer or film formed on a surface thereof.

In the specification, the term "surface of a substrate" used herein may mean an exposed surface of a substrate itself, or an external surface, such as a certain layer or film formed on the substrate.

In the specification, the term "room temperature" or "ambient temperature" used herein may be about 20° C. to about 28° C., and may vary depending on the season.

In the specification, the term "heterocyclic" used herein may mean an aromatic or non-aromatic ring containing at least one heteroatom (e.g., in the ring). The aromatic or non-aromatic ring may be a 3-membered to 9-membered aromatic or non-aromatic ring containing at least one heteroatom in the ring.

In the specification, the term "carbon saturated" used herein (e.g., as a carbon saturated group) may mean radicals in which all bonds between carbons or carbon and another atom (e.g., hydrogen) are single bonds (e.g., an alkyl group, for example, a C1-C7 alkyl group).

In the specification, the term "carbon unsaturated" used herein (e.g., as a carbon unsaturated group) may mean radicals in which some or all of bonds between carbons are double bonds or triple bonds (e.g., an alkenyl group or an alkynyl group, for example, a C2-C7 alkenyl group or a C2-C7 alkynyl group).

In the specification, the term "alkyl" used herein may mean a monovalent straight chain or branched chain saturation hydrocarbon radical composed of carbon and hydrogen atoms.

In the specification, the term "alkenyl" used herein may mean straight chain or branched chain hydrocarbon radicals containing two to seven carbon atoms and one or more carbon and carbon double bonds.

In the specification, the term "cycloalkyl" used herein may mean alkyl radicals composed of at least one ring.

In the specification, the term "cycloalkenyl" used herein may mean alkenyl radicals composed of at least one ring. As used herein, the term "or" is not an exclusive term, e.g., "A or B" would include A, B, or A and B. Unless described otherwise, all substitutable groups may be substituted or unsubstituted.

According to an embodiment, a silicon compound may be represented by, e.g., the following Chemical Formula (1).

$$R1_m(OR2)_n(OR3)_{3-m-n}Si—O—SiR4_p(OR5)_q(OR6)_{3-p-q}$$ [Chemical Formula (1)]

In Chemical Formula (1), m, n, p, and q may each independently be, e.g., an integer of 0 to 3. In an implementation, m, n, p, and q may satisfy the following relations: $m+p \geq 1$, $m+n \leq 3$, and $p+q \leq 3$.

R1 may be or may include, e.g., a heterocyclic group.

R4 may be or may include, e.g., a heterocyclic group, a carbon saturated group, or a carbon unsaturated group.

R2, R3, R5, and R6 may each independently be or include, e.g., a hydrogen atom, a C1-C7 alkyl group, a C2-C7 alkenyl group, a C3-C7 cycloalkyl group, or a C3-C7 cycloalkenyl group.

In an implementation, in the silicon compound of Chemical Formula (1), R1 and R4 may each independently be, e.g., a heterocyclic group including a nitrogen (N) atom or an oxygen (O) atom.

In an implementation, in the silicon compound of Chemical Formula (1), R1 and R4 may each independently be, e.g., a heterocyclic group including: a carbon (C) atom and an N atom; a C atom and an O atom; or a C atom and a sulfur (S) atom. In an implementation, in the silicon compound of Chemical Formula (1), R1 and R4 may each independently be, e.g., a heterocyclic group including a C atom and an N atom, an O atom, or an S atom.

In an implementation, the silicon compound may be represented by, e.g., the following Chemical Formula (2).

[Chemical Formula (2)]

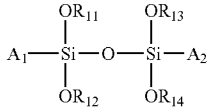

In Chemical Formula (2), $A_1$ may be or may include, e.g., C3-C9 heterocycloalkyl group including a N atom.

$A_2$ may be or may include, e.g., a C3-C9 heterocycloalkyl group including a N atom or a C1-C7 alkoxy group.

$R_{11}$, $R_{12}$, $R_{13}$, and $R_{14}$ may each independently be or include, e.g., a C1-C7 alkyl group.

In an implementation, in Chemical Formula (2), $A_1$ may be or may include, e.g., a 3-membered to 8-membered heterocycloalkyl group including a N atom.

In an implementation, $A_2$ may be or may include, e.g., a 3-membered to 8-membered heterocycloalkyl group including a N atom or a C1-C4 alkoxy group, and $R_{11}$, $R_{12}$, $R_{13}$, and $R_{14}$ are each independently a silicon compound of C1-C4 alkyl.

In an implementation, the silicon compound of Chemical Formula (1) may have a structure represented by, e.g., the following Compound (1).

[Compound (1)]

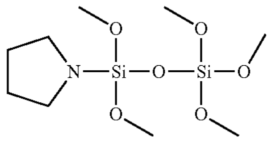

The silicon compound of Compound (1) may be indicated by the following Nomenclature (1).

Nomenclature (1)

1-Pyrrolidino-1,1,3,3,3-pentamethoxydisiloxane

In an implementation, the silicon compound of Chemical Formula (1) may have a structure represented by, e.g., the following Compound (2).

[Compound (2)]

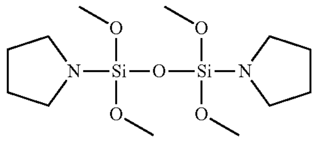

The silicon compound of Compound (2) may be indicated by the following Nomenclature (2).

Nomenclature (2)

1,3-Bis(Pyrrolidino)-1,1,3,3-tetramethoxydisiloxane

In an implementation, the silicon compound of Chemical Formula (1) may have a structure represented by, e.g., the following Compound (3).

[Compound (3)]

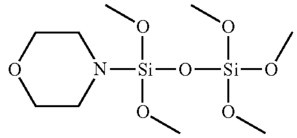

The silicon compound of Chemical Formula (1) may include a plurality of alkoxy groups. The alkoxy group may include, e.g., a methoxy group, an ethoxy group, a propyl group, an isopropyl group, a butoxy group, an isobutoxy group, an s-butoxy group, or a t-butoxy group.

In an implementation, the silicon compound may have a relatively high process temperature and relatively high thermal stability, and may provide excellent reactivity as a silicon precursor for forming a silicon-containing film. The relatively high process temperature may mean a case in which a process temperature of a substrate is within a range of, e.g., about 550° C. to about 650° C.

In an implementation, when a silicon-containing film is formed by using the silicon compound according to an embodiment, a high purity silicon-containing film that does not include a chlorine (Cl) element may be provided. In the case of other silicon-containing films that include a Cl element, due to a trap site formed by the Cl element, the degradation potential of time-dependent dielectric film breakdown (TDDB) properties could be very high. In an implementation, the silicon compound of Chemical Formula (1) may not include the Cl element, and the above issue may be addressed.

In an implementation, the silicon compound of Chemical Formula (1) may have a disiloxane basic structure in which the content of silicon atoms in the molecule is relatively high, and a relatively high deposition speed may be provided in a process of forming a silicon-containing film.

The silicon compound according to an embodiment may be synthesized by applying suitable organic chemical reactions, e.g., described below.

The silicon compound according to an embodiment may be used as a raw material suitable for an atomic layer deposition (ALD) process. In an implementation, the silicon compound may be used as a precursor suitable for a thermal ALD or plasma enhanced ALD (PEALD) process.

An embodiment provides a composition for depositing a silicon-containing film including the silicon compound.

The silicon compound may be represented by Chemical Formula (1), e.g., Chemical Formula (2).

An embodiment may provide a method of manufacturing a silicon-containing film by using the silicon compound described above.

In an implementation, a method of manufacturing a silicon-containing film may include, e.g., forming, on a substrate in a reaction space, a silicon compound adsorption layer of the silicon compound of Chemical Formula (1); and providing a reaction gas onto the silicon compound adsorption layer.

One or more embodiments may provide the silicon compound and a method of manufacturing an integrated circuit device by using a composition for depositing a silicon-containing film using the silicon compound.

FIG. 1 is a flowchart showing a method of manufacturing an integrated circuit device, according to an embodiment.

Referring to FIG. 1, a method S10 of manufacturing an integrated circuit device may include a process order of first and second operations S110 and S120.

In the first operation S110, a substrate may be prepared. The substrate may include a semiconductor substrate, a silicon on insulator (SOI) substrate, quartz, glass, plastic, a metal containing film, an insulating film, or a combination thereof. In an implementation, the semiconductor substrate may include, e.g., Si, Ge, SiGe, GaP, GaAs, SiC, SiGeC, InAs, InP, or a combination thereof. The plastic may include, e.g., polyimide, polyethylene terephthalate, polyethylene naphthalate, poly methyl methacrylate, polycarbonate, polyether sulfone, polyester, or a combination thereof. The metal containing film may include, e.g., Ti, TiN, Ta, TaN, Co, Ru, Zr, Hf, La, W, or a combination thereof.

In the second operation S120, a silicon-containing film may be formed on the substrate by using the composition for forming a silicon-containing film including the silicon compound of Chemical Formula (1).

The composition for forming a silicon-containing film may include a silicon compound according to an embodiment. In an implementation, the composition for forming a silicon-containing film may include a silicon compound represented by Chemical Formula (1) described above.

In an implementation, a silicon-containing film, that may be formed according to the method of manufacturing an integrated circuit device, may include, e.g., a silicon oxide ($SiO_2$) film.

In the second operation S120, an ALD process may be used to form a silicon-containing film. The composition for forming a silicon-containing film including the silicon compound may be used suitably for a chemical deposition process, e.g., the ALD process.

In an implementation, when the composition for forming a silicon-containing film is introduced into a deposition apparatus, the composition for forming a silicon-containing film may be introduced into a reaction chamber in which a substrate is placed, in a vapor state by vaporization, with a transfer gas, e.g., argon, nitrogen, helium, or the like, used as necessary.

In an implementation, when the composition for forming a silicon-containing film is introduced into a deposition apparatus, the composition for forming a silicon-containing film may be transferred to a vaporization chamber in a liquid or solution state, vaporized to a vapor state in the vaporization chamber by heating and/or decompression, and introduced into the reaction chamber.

In the second operation S120, a process of forming a silicon-containing film may include, e.g., a process of vaporizing a composition for forming a silicon-containing film including the silicon compound of Chemical Formula (1) and introducing the vaporized composition to a reaction chamber where a substrate is placed, and depositing the silicon compound on a surface of the substrate to form a silicon precursor thin film on the substrate; and a process of forming a silicon-containing film on the surface of the substrate by reacting the silicon precursor thin film with a reaction gas.

The reaction gas is a gas reacting with a silicon precursor thin film. In an implementation, the reaction gas may include, e.g., an oxidizing gas, a reducing gas, or a nitrifying gas. The oxidizing gas may include, e.g., $O_2$, $O_3$, $O_2$ plasma, $H_2O$, $NO_2$, NO, nitrous oxide ($N_2O$), CO, $CO_2$, $H_2O_2$, HCOOH, $CH_3COOH$, $(CH_3CO)_2O$, alcohol, peroxide, sulfur oxide, or a combination thereof. The reducing gas may include, e.g., hydrogen gas ($H_2$). The nitrifying gas may include, e.g., $NH_3$, $N_2$ plasma, organic amine compounds, such as monoalkyl amine, dialkylamine, trialkylamine, alkylenediamine, or the like, a hydrazine compound, or a combination thereof. For example, the reaction gas may include oxygen, hydrogen, vapor, hydrogen peroxide, ozone, a hydrazine compound, or a combination thereof.

In the second operation S120, in the forming of a silicon-containing film, deposition conditions may be controlled according to the thickness of a desired silicon-containing film and the thermal properties of a silicon compound used as a raw material. In an implementation, the deposition conditions may include the input flow rate of a composition for forming a silicon-containing film, the input flow rate of a transfer gas, the input flow rate of a reaction gas, a pressure, a reaction temperature, e.g., a substrate temperature, or the like.

In the second operation S120, in the forming of a silicon-containing film, the thin film thickness of a silicon-containing film may be adjusted by adjusting the number of cycles of an ALD process. The process of forming a silicon-containing film on the substrate by using an ALD process may include, e.g., a process of introducing, into a reaction chamber, vapor obtained by vaporizing a composition for forming a silicon-containing film including a silicon compound according to an embodiment; a process of forming a silicon precursor thin film on the surface of the substrate by using the vapor; a process of exhausting an unreacted raw material gas remaining in the reaction space on the substrate; and a process of forming a silicon-containing film on the surface of the substrate by chemically reacting the silicon precursor thin film with a reaction gas.

Figure 2:
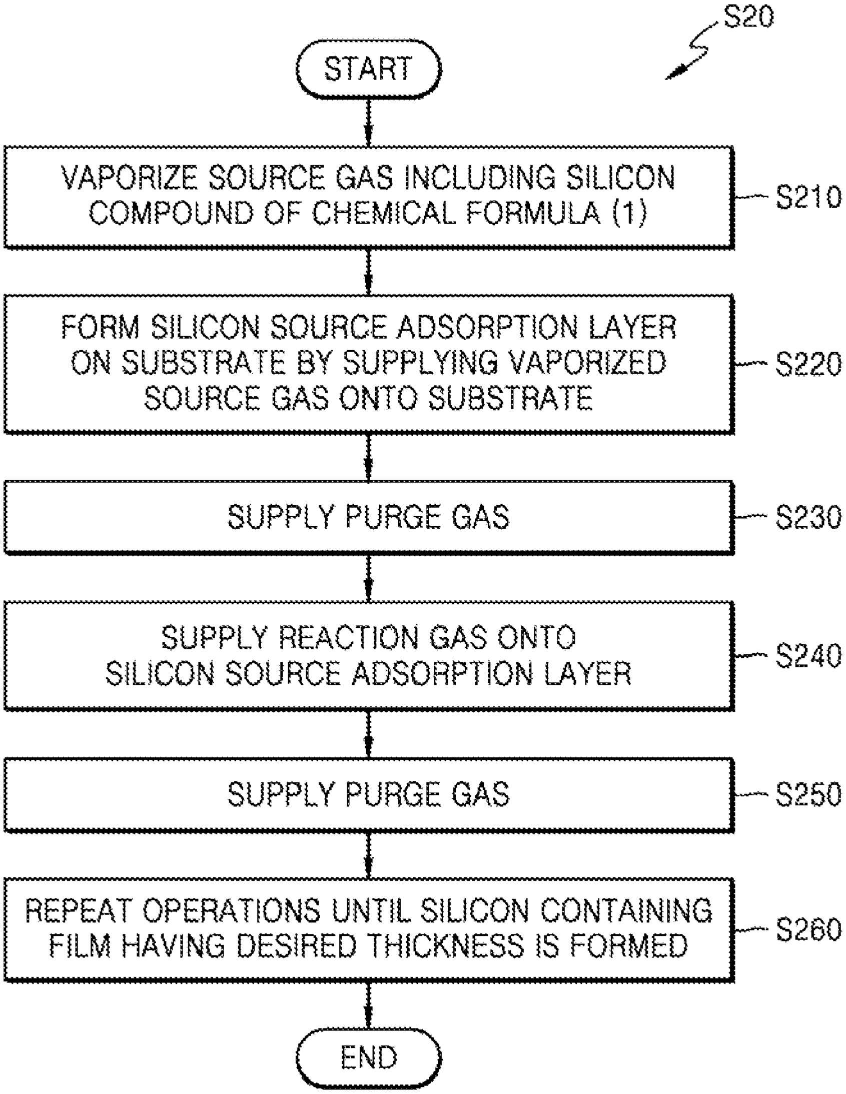
FIG. 2 is a flowchart showing in detail a method of forming a silicon-containing film according to a method of manufacturing an integrated circuit device, according to an embodiment.

FIG. 2 is a flowchart showing in detail a method of forming a silicon-containing film according to a method of manufacturing an integrated circuit device, according to an embodiment.

Referring to FIG. 2, a method S20 of manufacturing an integrated circuit device may include a process order of first to sixth operations S210 to S260.

In the first operation S210, a source gas including a silicon compound having the structure of Chemical Formula (1) may be vaporized.

In an implementation, the source gas may include the composition for forming a silicon-containing film described above. A process of vaporizing the source gas may be performed at, e.g., about 120° C. When the source gas is vaporized, the pressure in a raw material container or a vaporization chamber may be, e.g., about 1 Pa to about 10,000 Pa.

In the second operation S220, a vaporized source gas may be supplied onto the substrate to form a silicon source adsorption layer on the substrate. In an implementation, a reaction temperature may be, e.g., about 550° C. to about 650° C.

By supplying the vaporized source gas onto the substrate, an adsorption layer including a chemisorbed layer and a physisorbed layer of the vaporized source gas may be formed on the substrate. The chemisorbed layer of the vaporized source gas may constitute the silicon source adsorption layer.

In the third operation S230, unnecessary by-products on the substrate may be removed by supplying a purge gas onto the substrate. In an implementation, an inert gas, e.g., Ar, He, Ne, or the like, or a nitrogen gas ($N_2$), or the like may be used as the purge gas.

In an implementation, in lieu of a purge process, exhaustion may be performed by decompressing the reaction space where the substrate is placed. For the decompression, the pressure of the reaction space may be maintained to be, e.g., about 0.01 Pa to about 300 Pa.

In the fourth operation S240, a silicon-containing film in units of atomic layers may be formed by supplying the reaction gas onto the silicon source adsorption layer formed on the substrate.

In an implementation, when a silicon oxide film is formed on the substrate, the reaction gas may include an oxidizing gas, e.g., $O_2$, $O_3$, $O_2$ plasma, $H_2O$, $NO_2$, NO, nitrous oxide ($N_2O$), CO, $CO_2$, $H_2O_2$, HCOOH, $CH_3COOH$, $(CH_3CO)_2O$, alcohol, peroxide, sulfur oxide, or a combination thereof. In an implementation, the reaction gas may include a reducing gas, e.g., $H_2$ gas.

While performing the fourth operation S240, a high temperature state may be maintained so that the silicon source adsorption layer and the reaction gas sufficiently react with each other. In an implementation, the reaction gas may be plasma-processed. In an implementation, a high frequency (RF) output during the plasma processing may be, e.g., about 0 W to about 1,500 W.

In the fifth operation S250, unnecessary by-products on the substrate may be removed by supplying a purge gas onto the substrate. In an implementation, an inert gas, e.g., Ar, He, Ne, or the like, a $N_2$ gas, or the like may be used as the purge gas.

In the sixth operation S260, until a silicon-containing film having a desired thickness is formed, the first to fifth operations S210 to S250 described above may be repeatedly performed.

In the method S20 of manufacturing an integrated circuit device, as a thin film forming process including a series of processes is set to be one cycle, the cycle may be repeated multiple times until a silicon-containing film having a desired thickness is formed. In an implementation, after performing one cycle, by performing an exhaust process using the purge gas similarly in the third operation S230 or the fifth operation S250, unreacted gases may be exhausted from the reaction chamber, and then a subsequent cycle may be performed.

In an implementation, various modifications and changes may be made to the method of manufacturing an integrated circuit device.

In an implementation, to form a silicon-containing film on the substrate, the silicon compound having the structure of Chemical Formula (1) may be supplied onto the substrate together with or sequentially with at least one of the precursor, the reaction gas, the transfer gas, and the purge gas. Detailed configurations of the other precursor, the reaction gas, the transfer gas, and the purge gas that may be supplied onto the substrate with the silicon compound having the structure of Chemical Formula (1) may be as described above.

The silicon-containing film formed by the method according to an embodiment may be used as a material for various constituent elements constituting an integrated circuit device. In an implementation, the silicon-containing film may be used as a material forming a gate insulating film constituting a logic device or a memory device. The logic device may include a central processing unit (CPU), a controller, an application specific integrated circuit (ASIC), or the like. The memory device may include volatile memory devices, such as dynamic random access memory (DRAM) or static random access memory (SRAM), or non-volatile memory devices, such as phase-change random access memory (PRAM), magnetoresistive random access memory (MRAM), ferroelectric random access memory (FeRAM), or resistive random access memory (RRAM).

FIGS. 3 to 6 are views showing an integrated circuit device including a silicon-containing film manufactured according to the method of manufacturing an integrated circuit device, according to an embodiment.

Figure 3:
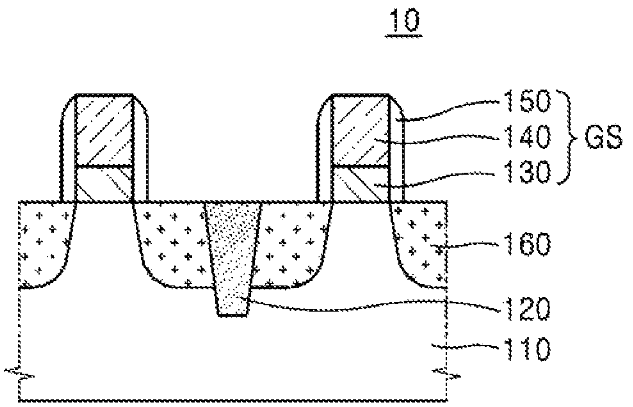
FIGS. 3 to 6 are views showing integrated circuit devices including a silicon-containing film manufactured according to the method of manufacturing an integrated circuit device, according to an embodiment.

Referring to FIG. 3, an integrated circuit device 10 may include a substrate 110, a device separation film 120, a gate structure GS, and source/drain regions 160.

In the integrated circuit device 10 of the present embodiment, the substrate 110 may be substantially the same as that described above with reference to FIG. 1.

The device separation film 120 may be formed as one insulating film, or may include an outer insulating film and an inner insulating film. The outer insulating film and the inner insulating film may be formed of different materials. In an implementation, the outer insulating film may include an oxide film, and the inner insulating film may include a nitride film. In an implementation, an active area may be defined in the substrate 110 by the device separation film 120.

The gate structure GS may include a gate dielectric film 130, a gate electrode 140, and a spacer 150.

The gate dielectric film 130 may be formed by an ALD process by using the silicon compound represented by Chemical Formula (1) described above. In an implementation, the gate dielectric film 130 may have excellent time-dependent dielectric film breakdown properties and high insulating strength properties.

The gate electrode 140 may include one gate film, or may be formed in a multilayer. In an implementation, the gate electrode 140 may include, e.g., an impurity-doped semiconductor, a metal, a conductive metal nitride, or a metal silicide.

The spacer 150 may be formed on side walls of the gate dielectric film 130 and the gate electrode 140. The spacer 150 may include a silicon oxide, a silicon nitride, or a silicon oxynitride. In an implementation, the spacer 150 may be formed in a single layer, or the spacer 150 may be formed in a dual layer or a triple layer.

The source/drain regions 160 may be respectively formed in the substrate 110 at both sides of the gate structure GS, and a channel region may be defined below the gate structure GS and between the source/drain regions 160.

Figure 4:
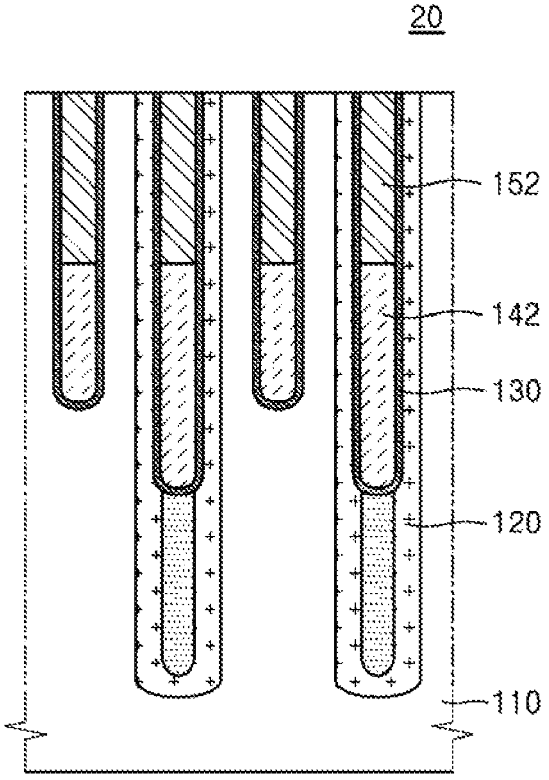

Referring to FIG. 4, an integrated circuit device 20 may include, e.g., the substrate 110, the device separation film 120, the gate dielectric film 130, a word line 142, and a buried insulating film 152.

In the integrated circuit device 20 of the present embodiment, the substrate 110 and the device separation film 120 may be substantially the same as those described above with reference to FIG. 3. The gate dielectric film 130, the word line 142, and the buried insulating film 152 are sequentially formed in the active area of the substrate 110.

The gate dielectric film 130 may be formed by an ALD process by using the silicon compound represented by Chemical Formula (1) described above. In an implementation, the gate dielectric film 130 may have excellent time-dependent dielectric film breakdown properties and high insulating strength properties.

The word line 142 may include, e.g., Ti, TiN, Ta, TaN, W, WN, TiSiN, or WSiN.

The buried insulating film 152 may include, e.g., a silicon oxide film, a silicon nitride film, a silicon oxynitride film, or a combination thereof.

A plurality of word lines 142 extending parallel to each other in a first direction may be in the active area of the substrate 110. The word lines 142 may be arranged at regular intervals. The width or interval of the word lines 142 may be determined according to a design rule. A plurality of bit lines extending parallel to each other in a second direction orthogonal to the first direction may be above the word lines 142. The bit lines may also be arranged at regular intervals.

Figure 5:
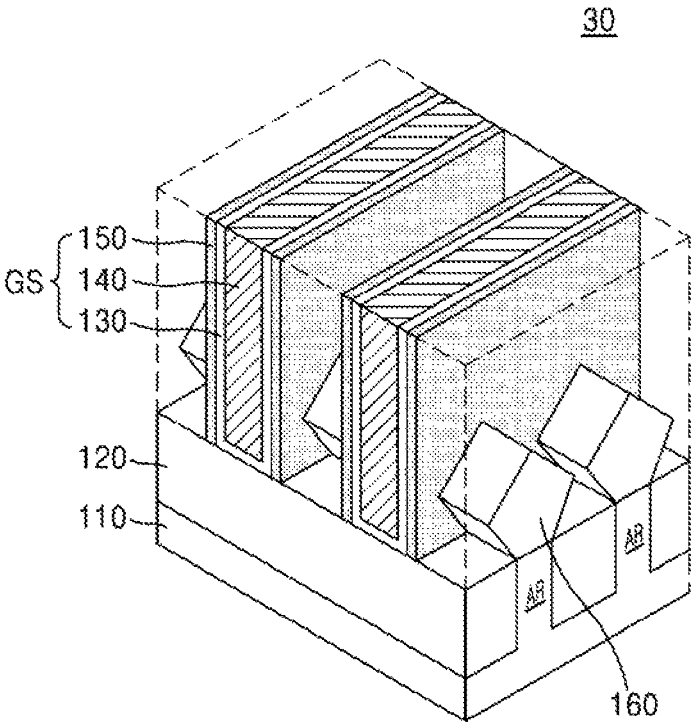

Referring to FIG. 5, an integrated circuit device 30 may include, e.g., the substrate 110 including a fin-type active area AR, the device separation film 120, the gate dielectric film 130, the gate electrode 140, and the spacer 150.

In the integrated circuit device 30 of the present embodiment, the materials forming the substrate 110 and the device separation film 120 may be substantially the same as those described above with reference to FIG. 3. In an implementation, the integrated circuit device 30 may include a plurality of fin-type active areas AR protruding from the substrate 110 and extending in the first direction. The device separation film 120 may expose an upper area of the fin-type active area AR.

The gate dielectric film 130, the gate electrode 140, and the spacer 150 may be substantially the same as those described above with reference to FIG. 3. The gate dielectric film 130 may be formed by an ALD process by using the silicon compound represented by Chemical Formula (1) described above. In an implementation, the gate dielectric film 130 may have excellent time-dependent dielectric film breakdown properties and high insulating strength properties. The gate structure GS may extend in in the second direction crossing the fin-type active area AR.

The source/drain regions 160 may be respectively in the fin-type active areas AR at both sides of the gate structure GS. The source/drain regions 160 may be spaced apart from each other with the gate structure GS therebetween. The source/drain regions 160 may include a selective epitaxial growth layer formed by using the fin-type active area AR as a seed.

Figure 6:
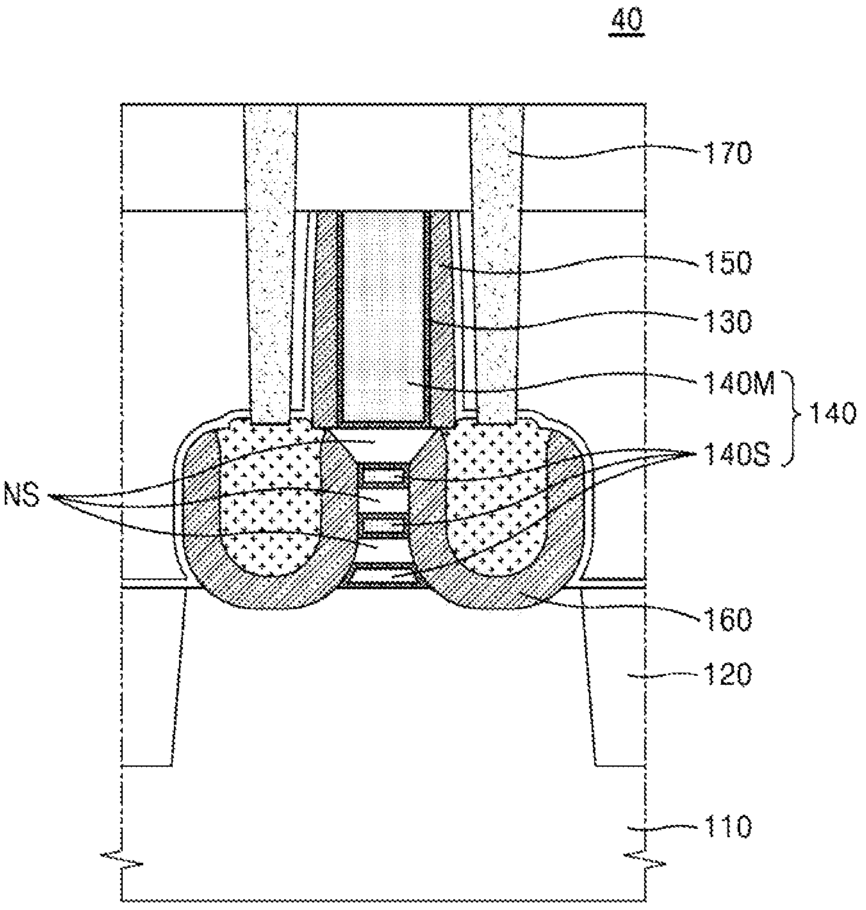

Referring to FIG. 6, an integrated circuit device 40 may include, e.g., the substrate 110 including a fin-type active area, the device separation film 120, the gate dielectric film 130, the gate electrode 140 including a main gate electrode 140M and a sub-gate electrode 140S, the spacer 150, and a contact structure 170.

In the integrated circuit device 40 of the present embodiment, the materials forming the substrate 110 and the device separation film 120 may be substantially the same as those described above with reference to FIG. 3. In an implementation, the integrated circuit device 40 may include a plurality of fin-type active areas protruding from the substrate 110 and extending in the first direction. The device separation film 120 may expose an upper area of the fin-type active area.

A plurality of semiconductor patterns NS may be arranged apart from each other in a direction perpendicular to an upper surface of the substrate 110 in the fin-type active area. The semiconductor patterns NS may have a shape of, e.g., a nanosheet.

The gate electrode 140 may surround the semiconductor patterns NS and may be on the fin-type active area and the device separation film 120. The gate electrode 140 may include the main gate electrode 140M and a plurality of sub-gate electrodes 140S.

The gate dielectric film 130 may be between the gate electrode 140 and the semiconductor patterns NS. The gate dielectric film 130 may be conformally arranged on the upper surface and the side walls of the semiconductor patterns NS. The gate dielectric film 130 may be formed by an ALD process by using the silicon compound represented by Chemical Formula (1) described above. In an implementation, the gate dielectric film 130 may have excellent time-dependent dielectric film breakdown properties and high insulating strength properties.

The source/drain regions 160 may include a selective epitaxial growth layer formed by using the fin-type active area as a seed.

In an implementation, the integrated circuit devices 10, 20, 30, and 40 including the silicon-containing film manufactured according to the method of manufacturing an integrated circuit device, according to an embodiment, may be applied in various ways.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, specific synthesis examples and silicon oxide film formation examples of a silicon compound according to embodiments are described.

In the synthesis examples described below, an ALD process was performed by using atomic layer deposition equipment including a typical vertical furnace. Furthermore, with respect to silicon-containing films obtained from specific silicon-containing film formation examples described below, a thickness thereof was measured by using an ellipsometer, and thin film properties were analyzed by using X-ray photoelectron spectroscopy. Furthermore, wet etching resistance of the obtained silicon-containing films was evaluated.

(1) Synthesis Example 1

Synthesis of
1-Pyrrolidino-1,1,3,3,3-pentamethoxydisiloxane

Under an anhydrous and inert atmosphere, 7.02 g (0.05 mol) of aluminum trichloride ($AlCl_3$) was added to a flame-dried 2,000 ml flask, and 800 g (3.09 mol) of hexamethoxydisiloxane ($((CH_3O)_3Si)_2O$) and 174.1 g (1.02 mol) of silicontetrachloride ($SiCl_4$) were sequentially added thereto at ambient temperature, and then agitated for three days at ambient temperature.

$AlCl_3$ was filtered and removed, and trichloromethoxysilane ($SiCl_3OCH_3$) generated after a reaction was removed under reduced pressure. In this process, recovered 1-chloro-1,1,3,3,3-pentamethoxydisiloxane ($Cl(CH_3O)_2SiOSi(OCH_3)_3$) was mixed with n-hexane and agitated triethylamine ($C_2H_5N$) 469 g (4.63 mol) was added thereto, and then 329.6 g (4.63 mol) of pyrrolidine ($(CH_2)_4NH$) was slowly added thereto while maintaining a temperature of −25° C.

After the addition was complete, the temperature of the reaction solution was slowly increased to ambient temperature, and the solution was agitated for three hours at ambient temperature. After the agitation, triethylamine chloride hydrogen salt ($C_2H_5NHCl$) was removed therefrom through filtering, a solvent was removed from an obtained solution under reduced pressure, and 250 g (0.84 mol) of 1-pyrrolidino-1,1,3,3,3-pentamethoxydisiloxane ($(CH_2)_4)N(CH_3O)_2SiOSi(CH_3O)_3$) was obtained (yield 54%) through decompression distillation in which at 0.639 torr a temperature of 61° C. was maintained.

$^1$H-NMR ($C_6D_6$): δ 1.65 (m, 4H $(CH_2)_2$), 2.98 (m, 4H, $(SiN(CH_2)_2)$, 3.50 (s, 6H $(N(CH_3O)_2Si)$, 3.55 (S, 9H $(OSi(OCH_3)_3)$ $^{29}$Si-NMR ($C_6D_6$): δ −73.6 ($(((CH_2)_4)N(CH_3O)_2SiO)$, −85.9 ($(OSi(OCH_3)_3)$)

(2) Synthesis Example 2

Synthesis of 1,3-bis(Pyrrolidino)-1,1,3,3-tetramethoxydisiloxane

Under an anhydrous and inert atmosphere, 432 g (1.67 mol) of hexamethoxydisiloxane ($((CH_3O)_3Si)_2O$) and 189.7 g (1.11 mol) of silicontetrachloride ($SiCl_4$) were sequentially added to a flame-dried 2,000 ml stainless steel high pressure reactor at ambient temperature, and then the solution was agitated for two days at 160° C. while maintaining a pressure of 1.6 bar.

Dichlorodimethoxysilane ($SiCl_2(OCH_3)_2$) generated after the reaction was removed therefrom under reduced pressure. In this process, recovered 1,3-bis-chloro-1,1,3,3-tetramethoxydisiloxane ($Cl(CH_3O)_2SiOSi(OCH_3)_2Cl$) was mixed with n-hexane and then agitated, and after adding 460 g (4.54 mol) of triethylamine ($C_2H_5N$) thereto, 323 g (4.54 mol) of pyrrolidine ($(CH_2)_4NH$) was slowly added thereto while maintaining a temperature of −25° C.

After the addition was complete, the temperature of a reaction solution was slowly increased to ambient temperature, and the reaction solution was agitated for three hours at ambient temperature. After the agitation, triethylamine chloride hydrogen salt ($C_2H_5NHCl$) was removed through filtering, a solvent was removed from an obtained solution under reduced pressure, and 200 g (0.59 mol) of 1,3-bis(pyrrolidino)-1,1,3,3-tetramethoxydisiloxane ($(((CH_2)_4)N(CH_3O)_2Si)_2O$) was obtained (yield 40%) through decompression distillation in which at 0.45 torr at a temperature of 96° C. was maintained.

$^1$H-NMR ($CDCl_3$): δ 1.61 (m, 8H $(CH_2)_2$), 2.96 (m, 8H, $(SiN(CH_2)_2)$, 3.43 (s, 12H $(N(CH_3O)_2Si)_2O$)

$^{29}$Si-NMR ($CDCl_3$): δ −73.8 ($(((CH_2)_4)N(CH_3O)_2Si)_2O$)

Figure 7:
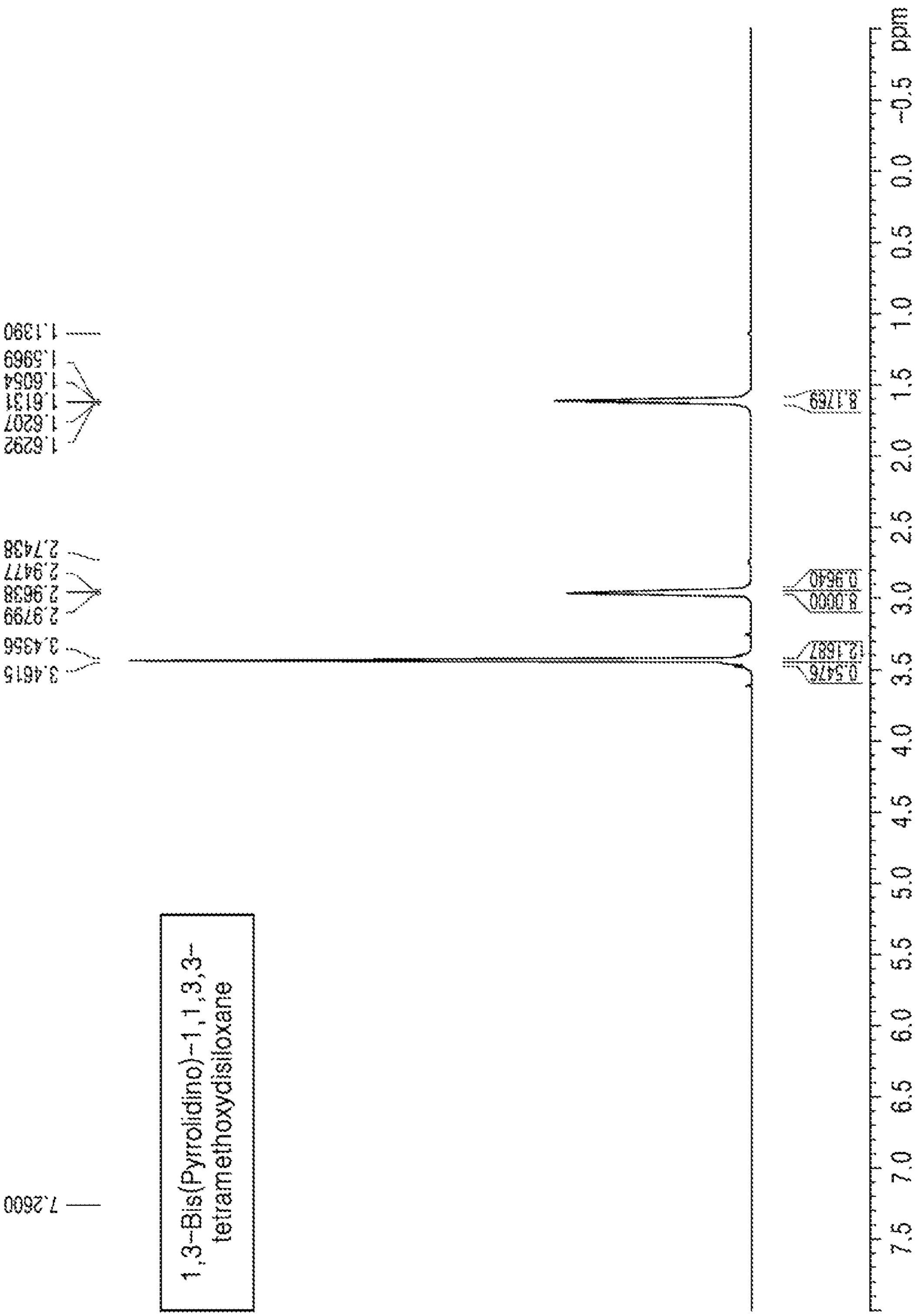
FIG. 7 is a graph showing a $^1$H-nuclear magnetic resonance (NMR) spectrum of a silicon compound according to an embodiment.

Evaluation of a compound with respect to Synthesis Example 2 is illustrated in the drawings. FIG. 7 is a graph showing a nuclear magnetic resonance (NMR) spectrum of a silicon compound according to an embodiment, FIG. 8 is a graph showing a thermogravimetric analysis result of a silicon compound according to an embodiment, and FIG. 9 is a graph showing a differential scanning calorimetry (DSC) analysis result of a silicon compound according to an embodiment.

Figure 8:
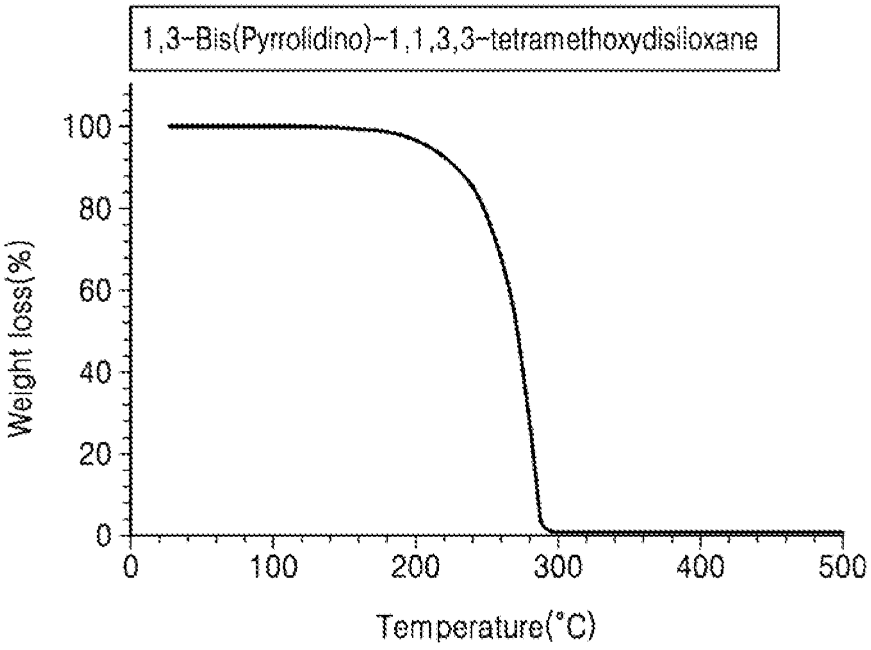
FIG. 8 is a graph showing a thermogravimetric analysis result of a silicon compound according to an embodiment.
Figure 9:
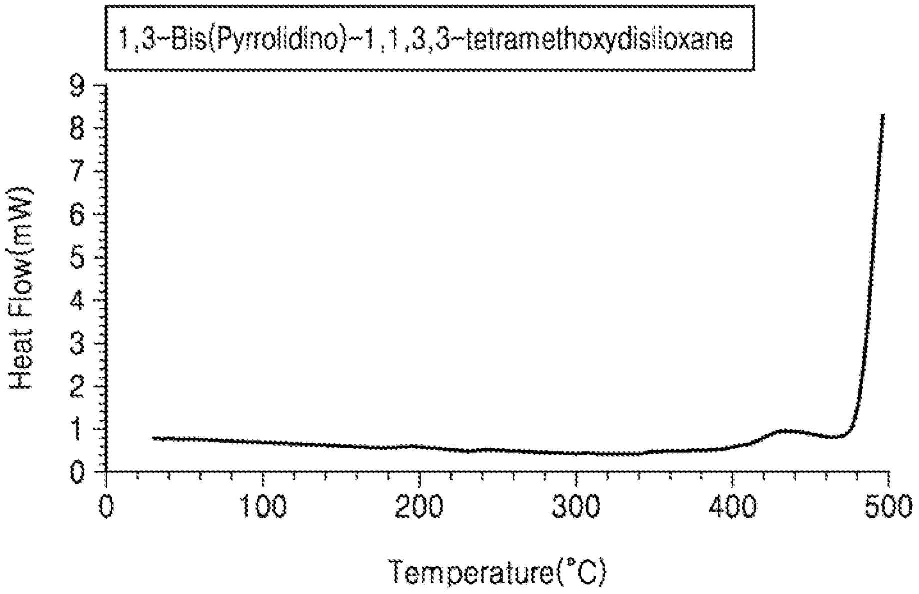
FIG. 9 is a graph showing a differential scanning calorimetry (DSC) analysis result of a silicon compound according to an embodiment.

As illustrated in FIGS. 8 and 9, it may be seen from a result of Synthesis Example 2 that the silicon compounds according to an embodiment exhibit excellent vapor pressure.

(3) Silicon Oxide Film Formation Example 1

Deposition of a Silicon Oxide Film by an ALD Process

In an atomic layer deposition apparatus configured as a typical vertical furnace using an ALD process, a thin film evaluation like an ALD window (550° C. to 650° C.) evaluation was performed by using 1-pyrrolidino-1,1,3,3,3-pentamethoxydisiloxane (the compound of Synthesis Example 1), as a composition for depositing a silicon-containing film for forming a silicon oxide film.

As such, a temperature range enabling the ALD process is referred to as an ALD window, and the range of the ALD window depends on a silicon compound. During an ALD window evaluation, the temperature of a substrate was set to be in a range of 550° C. to 650° C., and a silicon precursor was filled in a stainless steel bubbler container and maintained at 120° C.

$O_2$ gas and $H_2$ gas were used as reaction gases, and $N_2$ gas was used as a purge gas.

Process (1): The silicon precursor of Synthesis Example 1 vaporized in the stainless steel bubbler container was transferred to the substrate for about 5 seconds by using $N_2$ gas supplied at a flow rate of 100 sccm, as a transfer gas, and adsorbed on the substrate.

Process (2): The unadsorbed silicon precursor was removed for about 30 seconds by using $N_2$ gas supplied at a flow rate of 2,000 sccm as a purge gas.

Process (3): A silicon oxide film was formed for about 10 seconds by using $O_2$ gas supplied at a flow rate of 3,500 sccm and $H_2$ gas supplied at a flow rate of 1,200 sccm, as reaction gases.

Process (4): Reaction by-products and a residual reaction gas were removed for about 5 seconds by using $N_2$ gas supplied at a flow rate of 2,000 sccm, as a purge gas.

By repeating a plurality of cycles, one cycle being the processes (1) to (4), a silicon oxide film was formed to a certain thickness.

Table 1 below shows detailed deposition conditions of a silicon oxide film.

TABLE 1

| Silicon Precursor | | 1-pyrrolidino-1,1,3,3,3-pentamethoxydisiloxane |
|---|---|---|
| Silicon Oxide Film Deposition Condition | | ALD Window |
| Substrate Temperature (° C.) | | 550-650 |
| Silicon Precursor | Heating Temperature (° C.) | 120 |
| | Injection Time (sec.) | 5 |
| Purge Gas | Flow Rate (sccm) | 2,000 |
| | Injection Time (sec.) | 30 |
| Reaction Gas and Plasma | Oxygen flow Rate (sccm) | 3,500 |
| | Hydrogen Flow Rate (sccm) | 1,200 |
| | Injection Time (sec.) | 10 |
| Purge Gas | Flow Tate (sccm) | 2,000 |
| | Injection Time (sec.) | 5 |
| Number of Depositions | Cycle | 80 |

The thickness of the deposited silicon oxide film was measured by using an ellipsometer, and silicon oxide film formation and the composition of the silicon oxide film were analyzed by using X-ray photoelectron spectroscopy, which are shown in Table 2 and Table 3 below.

The thickness, growth speed, and refractive index of a deposited silicon oxide film through ellipsometer analysis are shown in Table 2. As the thickness of a thin film is very thin within about 100 Å, the refractive index is fixed to a value of 1.48.

TABLE 2

| Reaction Gas | Substrate Temperature (° C.) | Thin Film Thickness (Å) | Growth Speed (Å/cycle) | Refractive Index |
|---|---|---|---|---|
| Oxygen Gas and Hydrogen Gas | 550 | 106 | 1.33 | 1.48 |
| | 600 | 110 | 1.38 | 1.48 |
| | 650 | 119 | 1.49 | 1.48 |

During the ALD window evaluation according to the substrate temperature analyzed by using the X-ray photoelectron spectroscopy, with respect to the composition of a silicon oxide film, the composition of a thin film (at %) is summarized in Table 3 below with a content amount value for each atom. As a result, it was determined that there was no C, N, and chlorine (Cl) in the silicon oxide film, and that even when the substrate temperature increases, the silicon/oxygen ratio in the silicon oxide film was almost constant.

TABLE 3

| Substrate Temperature (° C.) | Composition of Thin Film (at %) C | N | Cl | Si | O | Si/O Ratio |
|---|---|---|---|---|---|---|
| 550 | 0 | 0 | 0 | 35.0 | 65.0 | 0.54 |
| 600 | 0 | 0 | 0 | 34.8 | 65.2 | 0.53 |
| 650 | 0 | 0 | 0 | 34.7 | 65.3 | 0.53 |

Furthermore, wet etching resistance analysis of the deposited silicon oxide film was conducted. Dilute hydrofluoric acid ($H_2O$:HF=200:1) was used as an etchant. A wet etching rate of the silicon oxide film was 1.8 Å/sec to 2.7 Å/sec, which is an excellent wet etching resistance, and was determined that, as the substrate temperature increased, the wet etching rate of the silicon oxide film decreases.

(4) Silicon Oxide Film Formation Example 2

Deposition of a Silicon Oxide Film by an ALD Process

In an atomic layer deposition apparatus configured as a typical vertical furnace using an ALD process, a thin film evaluation like a source feeding time saturation evaluation and an ALD window (550° C. to 650° C.) was performed by using 1,3-bis(pyrrolidino)-1,1,3,3-tetramethoxydisiloxane (the compound of Synthesis Example 2), as a composition for depositing a silicon-containing film for forming a silicon oxide film.

During the ALD window evaluation, a substrate temperature was set to be in a range of 550° C. to 650° C., and for the case of a source feeding time saturation evaluation, the substrate temperature was maintained at 600° C. The silicon precursor was filled in a stainless steel bubbler container and maintained at 120° C.

$O_2$ gas and $H_2$ gas were used as reaction gases, and $N_2$ gas was used as a purge gas.

Process (1): The silicon precursor of Synthesis Example 2 vaporized in the stainless steel bubbler container was transferred to the substrate for about 10 seconds by using $N_2$ gas supplied at a flow rate of 100 sccm, as a transfer gas, and adsorbed on the substrate. However, when the source feeding time saturation was evaluated, a range of about 5 sec. to about 30 sec. was applied differentially.

Process (2): The unadsorbed silicon precursor was removed for about 30 seconds by using $N_2$ gas supplied at a flow rate of 2,000 sccm as a purge gas.

Process (3): A silicon oxide film was formed for about 10 seconds by using $O_2$ gas supplied at a flow rate of 3,500 sccm and $H_2$ gas supplied at a flow rate of 1,200 sccm, as reaction gases.

Process (4): Reaction by-products and a residual reaction gas were removed for about 5 seconds by using $N_2$ gas supplied at a flow rate of 2,000 sccm, as a purge gas.

By repeating a plurality of cycles, one cycle being the processes (1) to (4), a silicon oxide film was formed to a certain thickness.

Table 4 below shows detailed deposition conditions of a silicon oxide film.

TABLE 4

| Silicon Precursor | | 1,3-Bis(pyrrolidino)-1,1,3,3-tetramethoxydisiloxane | |
|---|---|---|---|
| Silicon Oxide Film Deposition Condition | | ALD Window | Source Feed Saturation Time |
| Substrate Temperature (° C.) | | 550-650 | 600 |
| Silicon Precursor | Heating Temperature (° C.) | 120 | 120 |
| | Injection Time (sec.) | 20 | 5-30 |
| Purge Gas | Flow Rate (sccm) | 2,000 | 2,000 |
| | Injection Time (sec.) | 30 | 30 |
| Reaction Gas and Plasma | Oxygen Flow Rate (sccm) | 3,500 | 3,500 |
| | Hydrogen Flow Rate (sccm) | 1,200 | 1,200 |
| | Injection Time (sec.) | 10 | 10 |
| Purge Gas | Flow Rate (sccm) | 2,000 | 2,000 |
| | Injection Time (sec.) | 5 | 5 |
| Number of Depositions | Cycle | 100 | 100 |

The thickness of the deposited silicon oxide film was measured by using an ellipsometer, and silicon oxide film formation and the composition of the silicon oxide film were analyzed by using X-ray photoelectron spectroscopy, as shown in Table 5 and Table 6 below.

The thickness, growth speed, and refractive index of the deposited silicon oxide film through ellipsometer analysis are shown in Table 5. As the thickness of a thin film was very thin within about 100 Å, the refractive index is fixed to a value of 1.48.

Figure 10:
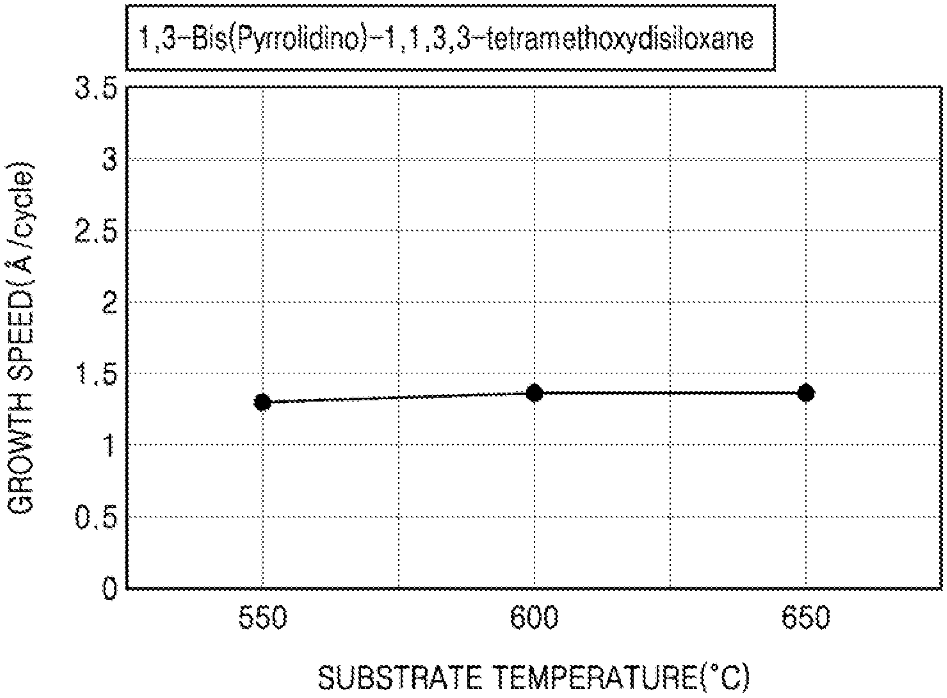
FIG. 10 is a graph showing a growth speed of a silicon-containing film obtained by using a silicon compound according to an embodiment.

FIG. 10 is a graph showing a growth speed according to the substrate temperature, when 1,3-bis(pyrrolidino)-1,1,3,3-tetramethoxydisiloxane was supplied, as a source, onto the substrate. Through FIG. 10 and Table 5 below, it is checked that the growth speed of a thin film is stably maintained at about 1.3 Å/cycle in a range of a relatively high substrate temperature of 550° C. to 650° C.

Furthermore, through Table 5 below, it was determined that properties of a high temperature ALD process appear, in which the growth speed of a thin film is saturated at about 1.34 Å/cycle as a source feeding time increases at a high temperature, e.g., 600° C.

TABLE 5

| Reaction Gas | Substrate Temperature (° C.) | Source Feed Time (sec.) | Thin Film Thickness (Å) | Growth Speed (Å/cycle) | Refractive Index |
|---|---|---|---|---|---|
| Oxygen Gas and Hydrogen Gas | 550 | 20 | 128 | 1.28 | 1.48 |
| | 600 | | 133 | 1.33 | 1.48 |
| | 650 | | 133 | 1.33 | 1.48 |
| Oxygen Gas and Hydrogen Gas | 600 | 5 | 58 | 0.73 | 1.48 |
| | | 10 | 90 | 1.13 | 1.48 |
| | | 20 | 133 | 1.33 | 1.48 |
| | | 30 | 134 | 1.34 | 1.48 |

During the ALD window evaluation according to the substrate temperature analyzed by using the X-ray photoelectron spectroscopy, with respect to the composition of a silicon oxide film, the composition of a thin film (at %) is summarized in Table 6 below with a content amount value for each atom. As a result, it was determined that there was no C, N, and Cl in the silicon oxide film, and that even when the substrate temperature increased, the silicon/oxygen ratio in the silicon oxide film was almost constant.

TABLE 6

| Substrate Temperature (° C.) | Composition of Thin Film (at %) C | N | Cl | Si | O | Si/O Ratio |
|---|---|---|---|---|---|---|
| 550 | 0 | 0 | 0 | 35.0 | 65.0 | 0.54 |
| 600 | 0 | 0 | 0 | 34.8 | 65.2 | 0.53 |
| 650 | 0 | 0 | 0 | 34.7 | 65.3 | 0.53 |

Furthermore, wet etching resistance analysis of the deposited silicon oxide film was conducted. Dilute hydrofluoric acid ($H_2O$:HF=200:1) was used as an etchant. A wet etching rate of the silicon oxide film was 1.8 Å/sec to 2.7 Å/sec, which is an excellent wet etching resistance, and it was determined that, as the substrate temperature increases, the wet etching rate of the silicon oxide film decreased.

(5) Properties of a Silicon Compound

As such, the silicon compound according to embodiments, when used as a silicon precursor for forming a silicon-containing film, may provide high thermal stability and excellent reactivity.

Furthermore, the silicon compound according to embodiments, having a relatively high content of silicon atoms in a molecule, may provide a relatively high deposition speed in a process of forming a silicon-containing film.

Furthermore, when forming a silicon-containing film using a silicon compound according to embodiments, a high purity silicon-containing film that does not include a Cl atom may be provided, and the obtained silicon-containing film may provide excellent physical properties and electrical properties.

Ultimately, by forming a silicon-containing film using a silicon compound according to embodiments, provided is a method of manufacturing an integrated circuit device which may improve electrical properties and product productivity.

By way of summation and review, raw material compounds to form a silicon-containing film may be used to provide a stable deposition process, may be easy to handle, and may have excellent thin film properties and excellent etch resistance properties during forming of the silicon-containing film. A silicon compound may be advantageous in terms of stability and mass productivity of a semiconductor manufacturing process.

One or more embodiments may provide a silicon compound used to form a silicon-containing film.

One or more embodiments may provide a silicon compound which may form a thin film having a uniform thickness and may be easily handled under a relatively high process temperature condition, and may have excellent thin film properties and excellent etch resistance properties when used as a raw material compound to form a silicon-containing film.

One or more embodiments may provide a method of manufacturing an integrated circuit device which may help improve electrical properties and product productivity, by forming a silicon-containing film having excellent quality by using a silicon compound that provides excellent stability and mass productivity of a manufacturing process.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A silicon compound represented by Chemical Formula (1):

$$R1_m(OR2)_n(OR3)_{3-m-n}Si—O—SiR4_p(OR5)_q(OR6)_{3-p-q},$$ Chemical Formula (1)

wherein, in Chemical Formula (1), m, n, p, and q are each independently an integer of 0 to 3, and satisfy the following relations m+p≥1, m+n≤3, and p+q≤3, R1 is a heterocyclic group, R4 is a heterocyclic group, a carbon saturated group, or a carbon unsaturated group, and R2, R3, R5, and R6 are each independently a hydrogen atom, a C1-C7 alkyl group, a C2-C7 alkenyl group, a C3-C7 cycloalkyl group, or a C3-C7 cycloalkenyl group, wherein at least one of R1 and R4 includes an N atom.

2. The silicon compound as claimed in claim 1, wherein, in Chemical Formula (1), R1 and R4 are each independently a heterocyclic group including a nitrogen atom or an oxygen atom.

3. The silicon compound as claimed in claim 1, wherein, in Chemical Formula (1), R1 and R4 are each independently a heterocyclic group including:

a carbon atom and a nitrogen atom;

a carbon atom and an oxygen atom; or a carbon atom and a sulfur atom.

4. The silicon compound as claimed in claim 1, wherein:

the silicon compound represented by Chemical Formula (1) is represented by Chemical Formula (2), Chemical Formula (2)

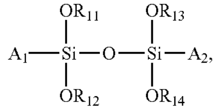

in Chemical Formula (2), $A_1$ is a C3-C9 heterocycloalkyl including a nitrogen atom, $A_2$ is a C1-C7 alkoxy group or a C3-C9 heterocycloalkyl including a nitrogen atom, and $R_{11}$, $R_{12}$, $R_{13}$, and $R_{14}$ are each independently a C1-C7 alkyl group.

5. The silicon compound as claimed in claim 4, wherein, in Chemical Formula (2):

$A_1$ is a 3-membered to 8-membered heterocycloalkyl group including a N atom, $A_2$ is a $C_1$-$C_4$ alkoxy group or a 3-membered to 8-membered heterocycloalkyl including a N atom, and $R_{11}$, $R_{12}$, $R_{13}$, and $R_{14}$ are each independently a $C_1$-$C_4$ alkyl group.

6. The silicon compound as claimed in claim 1, wherein the silicon compound represented by Chemical Formula (1) is Compound (1), Compound (2), or Compound (3):

Compound (1)

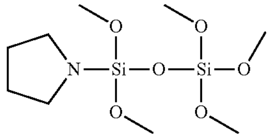

Compound (2)

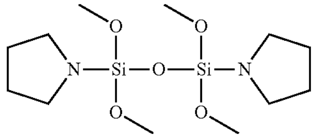

Compound (3)

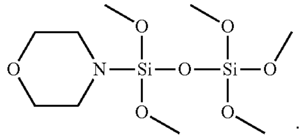

7. A composition for depositing a silicon-containing film, the composition comprising the silicon compound as claimed in claim 1.

8. A method of manufacturing an integrated circuit device, the method comprising forming a silicon-containing film on a substrate, by using a silicon compound represented by Chemical Formula (1):

$$R1_m(OR2)_n(OR3)_{3-m-n}Si—O—SiR4_p(OR5)_q(OR6)_{3-p-q},$$ Chemical Formula (1)

wherein, in Chemical Formula (1), m, n, p, and q are each independently an integer of 0 to 3, and satisfy the following relations: m+p≥1, m+n≤3, and p+q≤3, R1 is a heterocyclic group, R4 is a heterocyclic group, a carbon saturated group, or a carbon unsaturated group, and R2, R3, R5, and R6 are each independently a hydrogen atom, a C1-C7 alkyl group, a C2-C7 alkenyl group, a C3-C7 cycloalkyl group, or a C3-C7 cycloalkenyl group.

9. The method as claimed in claim 8, wherein forming the silicon-containing film includes:

forming, on a substrate in a reaction space, a silicon compound adsorption layer of the silicon compound represented by Chemical Formula (1); and providing a reaction gas onto the silicon compound adsorption layer.

10. The method as claimed in claim 9, wherein the reaction gas includes oxygen, hydrogen, vapor, hydrogen peroxide, ozone, a hydrazine compound, or a combination thereof.

11. The method as claimed in claim 8, wherein forming the silicon-containing film is performed when a surface temperature of the substrate is about 550° C. to about 650° C.

12. The method as claimed in claim 8, wherein the silicon-containing film includes a silicon oxide film.

13. The method as claimed in claim 8, wherein:

the silicon compound represented by Chemical Formula (1) is represented by Chemical Formula (2), Chemical Formula (2)

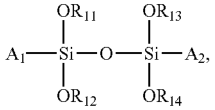

in Chemical Formula (2), $A_1$ is a C3-C9 heterocycloalkyl including a nitrogen atom, $A_2$ is a C1-C7 alkoxy group or a C3-C9 heterocycloalkyl including a nitrogen atom, and $R_{11}$, $R_{12}$, $R_{13}$, and $R_{14}$ are each independently a C1-C7 alkyl group.

14. The method as claimed in claim 8, wherein the silicon compound represented by Chemical Formula (1) is Compound (1), Compound (2), or Compound (3):

Compound (1)

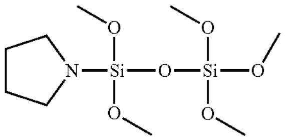

Compound (2)

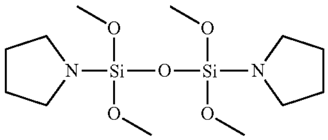

Compound (3)

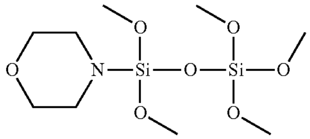

.

15. A method of manufacturing an integrated circuit device, the method comprising:

preparing a substrate having an active area and a device separation area;

forming a gate dielectric film on the substrate;

forming a gate electrode on the gate dielectric film;

forming a gate structure by patterning the gate dielectric film and the gate electrode; and forming source/drain regions in the substrate at both sides of the gate structure, wherein forming the gate dielectric film includes:

forming a silicon compound adsorption layer on a surface of the substrate by supplying a silicon compound represented by Chemical Formula (1) onto the substrate; and forming a silicon oxide film by supplying a reaction gas to a resultant in which the silicon compound adsorption layer is formed, $$R1_m(OR2)_n(OR3)_{3-m-n}Si—O—SiR4_p(OR5)_q(OR6)_{3-p-q},$$ Chemical Formula (1)

wherein, in Chemical Formula (1), m, n, p, and q are each independently an integer of 0 to 3, and satisfy the following relations: m+p≥1, m+n≤3, and p+q≤3, R1 is a heterocyclic group, R4 is a heterocyclic group, a carbon saturated group, or a carbon unsaturated group, and R2, R3, R5, and R6 are each independently a hydrogen atom, a C1-C7 alkyl group, a C2-C7 alkenyl group, a C3-C7 cycloalkyl group, or a C3-C7 cycloalkenyl group.

16. The method as claimed in claim 15, wherein, in Chemical Formula (1), R1 and R4 are each independently a heterocyclic group including a nitrogen atom or an oxygen atom.

17. The method as claimed in claim 15, wherein, in Chemical Formula (1), R1 and R4 are each independently a heterocyclic group including:

a carbon atom and a nitrogen atom;

a carbon atom and an oxygen atom; or a carbon atom and a sulfur atom.

18. The method as claimed in claim 15, wherein:

the silicon compound represented by Chemical Formula (1) is represented by

Chemical Formula (2)

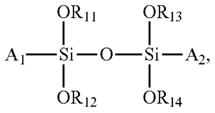

in Chemical Formula (2), $A_1$ is a C3-C9 heterocycloalkyl including a nitrogen atom, $A_2$ is a C1-C7 alkoxy group or a C3-C9 heterocycloalkyl including a nitrogen atom, and $R_{11}$, $R_{12}$, $R_{13}$, and $R_{14}$ are each independently a C1-C7 alkyl group.

19. The method as claimed in claim 18, wherein, in Chemical Formula (2):

$A_1$ is a 3-membered to 8-membered heterocycloalkyl group including a N atom, $A_2$ is a C1-C4 alkoxy group or a 3-membered to 8-membered heterocycloalkyl including a N atom, and $R_{11}$, $R_{12}$, $R_{13}$, and $R_{14}$ are each independently a C1-C4 alkyl group.

20. The method as claimed in claim 15, wherein the silicon compound represented by Chemical Formula (1) is Compound (1), Compound (2), or Compound (3):

Compound (1)

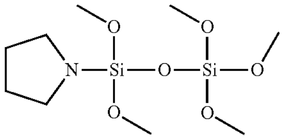

Compound (2)

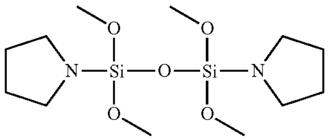

Compound (3)

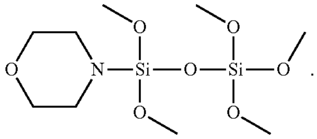

.

* * * * *